US006051373A

United States Patent [19]
Green et al.

[11] Patent Number: 6,051,373
[45] Date of Patent: Apr. 18, 2000

[54] METHODS FOR SCREENING FOR INHIBITORS OF THE TRANSCRIPTION-ENHANCING ACTIVITY OF THE X PROTEIN OF HEPATITIS B VIRUS

[75] Inventors: Michael R. Green, Boylston; Giovanni Perini, Worcester; James Lillie, Wellesley, all of Mass.

[73] Assignees: Scriptgen Pharmaceuticals, Inc., Waltham; University of Massachusetts Medical Center, Worcester, both of Mass.

[21] Appl. No.: 08/351,659

[22] Filed: Dec. 7, 1994

[51] Int. Cl.[7] ............................ C12Q 1/70; G01N 33/53; G01N 33/566
[52] U.S. Cl. .................................. 435/5; 435/7.8; 435/6; 436/501
[58] Field of Search .............................. 435/5, 6, 7.1, 7.8; 436/501, 518, 536; 530/324, 388.3, 388.85, 389.4; 536/23.1, 24.1

[56] References Cited

FOREIGN PATENT DOCUMENTS

| | | |
|---|---|---|
| WO-91/16429 | 10/1991 | WIPO . |
| WO-91/16456 | 10/1991 | WIPO . |
| WO-92/05286 | 4/1992 | WIPO . |
| WO-93/08701 | 5/1993 | WIPO . |
| WO-94/09133 | 4/1994 | WIPO . |
| WO-94/19473 | 9/1994 | WIPO . |
| WO-94/19494 | 9/1994 | WIPO . |

OTHER PUBLICATIONS

Avantaggiati et al., "The hepatitis B virus (HBV) pX trans-activates the c–fos promoter through multiple cis–acting elements", Oncogene 8, 1567–1574, 1993.
Kohler et al., "Towards Routine Diagnosis of Hepatitis B Virus DNA", Clin. Chem. 39, 1185, 1993.
Alber, *Curr.Biol.* 3:182, 1993.
Angel et al., *Biochim.Biophys. Acta 1072*:129, 1991.
Baum, *C&EN*, Feb. 7, 1994, pp. 20–26.
Benn et al., *Proc.Natl.Acad.Sci.USA. 91*:10350–10354, 1994.
Burley, *Curr.Opin.Struc.Biol. 4*:3–11, 1994.
Busch et al., *Trends Gen. 6*:36, 1990.
De–Medina et al., *Virol. 202*:401–407, 1994.
Ellenberger, *Curr.Opin.Struc.Biol. 4*:12, 1994.
E. Harlow & D. Lane, *Antibodies: A Laboratory Manual*, Cold Spring Harbor Laboratory, 1988.
Karin, *Trends Gen. 5*:65, 1989.
Kwee et al., *J. Virol. 66*:4382, 1992.
Maguire et al., *Science 252*:842–844, 1991.
Natoli et al., *Mol.Cell.Biol. 14*:989–998, 1994.
O'Neil et al., *Science 249*:774, 1990.
Patel et al., *Proc.Natl.Acad.Sci.USA 91*:7360, 1994.
Ponsetto et al., *Hepatology 14*:16–23, 1991.
Quadri, I. et al., *Proc.Natl.Acad.Sci. USA, 92*:1003–1007, 1995.
Sells et al., *J. Virol. 62*:2836, 1988.
Sells et al., *Proc.Natl.Acad.Sci.USA 84*:1005, 1987.
Takada et al., *Oncogene 9*:341–348, 1994.
Ziff, *Trends Gen. 6*:69, 1990.
Zola, *Monoclonal Antibodies: A Manual of Techniques*, CRC Press, Inc., Boca Raton, Florida, 1987.
Faktor et al., Oncogene, 5(6):867–872, Jun. 6, 1990.
Wagner et al., Science, 262:395–399, Oct. 15, 1993.
Williams et al., PNAS, 92(9):3819–3823.
Database WPI, Derwent Publication, Abstract No. 93–303964, Jul. 8, 1993.

*Primary Examiner*—Donna C. Wortman
*Assistant Examiner*—Jay Williams
*Attorney, Agent, or Firm*—Darby & Darby

[57] ABSTRACT

Disclosed is a method for screening for inhibitors of Hepatitis B Virus pX activity. The method involves contacting a test compound with (I) the pX protein of HBV, (ii) a transcription factor comprising the bZIP domain, or fragments that comprise a minimal a bZIP domain, and (iii) an oligoduplex comprising a target DNA sequence of the transcription factor to form a test mixture. After incubating the test mixture under appropriate conditions and for a sufficient time to allow pX-mediated dimerization and DNA binding of the transcription factor to occur, the level of DNA binding of the transcription factor in each test mixture is determined. A test compound is considered to be any compound that causes a decrease in the level of DNA binding in the test mixture relative to the level of DNA binding in control mixtures.

10 Claims, 9 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (ii) MOLECULE TYPE: DNA (genomic)

(vi) ORIGINAL SOURCE:
      (A) ORGANISM: Homo sapiens    (vii) IMMEDIATE SOURCE:
      (B) CLONE: CRE core    (xi) SEQUENCE DESCRIPTION: SEQ ID NO:1:

TCCTAAGTGA CGTCAGTGGA A                                    21

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear    (ii) MOLECULE TYPE: DNA (genomic)

(vi) ORIGINAL SOURCE:
      (A) ORGANISM: Homo sapiens    (vii) IMMEDIATE SOURCE:
      (B) CLONE: TRE site    (xi) SEQUENCE DESCRIPTION: SEQ ID NO:2:

AGCTTTGACT CATCCCGGA                                      19

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (ii) MOLECULE TYPE: DNA (genomic)

(vi) ORIGINAL SOURCE:
      (A) ORGANISM: Homo sapiens    (vii) IMMEDIATE SOURCE:
      (B) CLONE: C/EBP binding site    (xi) SEQUENCE DESCRIPTION: SEQ ID NO:3:

TGCAGATTGC GCAATCTGCA                                    20

(2) INFORMATION FOR SEQ ID NO:4:

(i) SEQUENCE CHARACTERISTICS:
      (A) LENGTH: 53 amino acids
      (B) TYPE: amino acid
      (C) STRANDEDNESS: Not Relevant
      (D) TOPOLOGY: linear    (ii) MOLECULE TYPE: peptide

```
    (v) FRAGMENT TYPE: internal (vi) ORIGINAL SOURCE:
        (A) ORGANISM: S. cerevisiae (vii) IMMEDIATE SOURCE:
        (B) CLONE: PEPTIDE BR-CC (xi) SEQUENCE DESCRIPTION: SEQ ID NO:4:

Ala Leu Lys Arg Ala Arg Asn Thr Glu Ala Ala Arg Arg Ser Arg Ala
  1               5                   10                  15

Arg Lys Leu Gln Arg Met Lys Gln Leu Glu Asp Val Lys Glu Leu Glu
                  20                  25                  30

Glu Lys Leu Lys Ala Leu Glu Glu Lys Leu Lys Ala Leu Glu Glu Lys
                  35                  40                  45

Leu Lys Ala Leu Gly
                  50

(2) INFORMATION FOR SEQ ID NO:5:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: linear (ii) MOLECULE TYPE: peptide (vi) ORIGINAL SOURCE:
        (A) ORGANISM: S. cerevisiae (vii) IMMEDIATE SOURCE:
        (B) CLONE: BR1SS (xi) SEQUENCE DESCRIPTION: SEQ ID NO:5:

Ala Leu Lys Arg Ala Arg Asn Thr Glu Ala Ala Arg Arg Ser Arg Ala
  1               5                   10                  15

Arg Lys Leu Gln Arg Met Lys Gln Gly Gly Cys
                  20                  25
```

METHODS FOR SCREENING FOR INHIBITORS OF THE TRANSCRIPTION-ENHANCING ACTIVITY OF THE X PROTEIN OF HEPATITIS B VIRUS

FIELD OF THE INVENTION

This invention pertains to methods for identifying compounds that are useful for inhibiting the transcription-enhancing activity of the Hepatitis B Virus (HBV) X protein. The invention also pertains to methods and compositions for inhibiting HBV replication and for treating HBV infection.

BACKGROUND OF THE INVENTION

Hepatitis B virus (HBV) is an important human pathogen that affects millions of people worldwide. HBV replicates predominantly in hepatocytes in vivo, resulting in either acute or chronic infection. While acute hepatitis is usually mild, in a substantial portion of infected people the virus is not cleared from the liver. These chronic carriers are at high risk for developing chronic hepatitis, liver cirrhosis, and hepatocarcinoma.

Several vaccines are available that reduce the risk of initial infection with HBV, but many individuals continue to become chronically infected with the virus. In addition, there is a large pool of existing chronic carriers—perhaps as many as 300 million worldwide—who are beyond treatment with vaccines. Development of effective methods and compositions for treatment of HBV infections is an important goal of the pharmaceutical industry. There is thus a need in the art for methods to identify new anti-HBV drugs that can be administered during and after exposure to this viral pathogen.

The HBV genome encodes only four major polypeptides: the surface antigen (S gene), the core antigen (C gene), the viral polymerase, and the X protein. The X protein, designated pX, which is expressed throughout the replication cycle of the virus, transcriptionally activates the HBV enhancer and is important for viral replication. HBV-induced malignant transformation may also require pX; in this case, functional pX is derived from a pX gene that has integrated into the genome of a hepatocyte.

Prior to the present invention, however, the mechanism by which pX activates viral transcription was unknown. Unlike most transcription factors, pX does not bind independently to DNA, and appears to act promiscuously via multiple transcription factors. pX has been reported to alter the DNA binding specificity of CREB and ATF2 (Maguire et al., Science 252:842–844, 1991); to activate Ras-GTP complex formation (Benn et al., Proc. Natl. Acad. Sci. USA 91:10350–10354, 1994); to cause the post-translational modification of c-Jun/c-fos (Natoli et al., Mol. Cell. Biol. 14:989–998, 1994); to possess intrinsic serine kinase activity; to act as a serine proteinase inhibitor (Takada et al., Oncogene 9:341–348, 1994); and to function as a ribo/deoxyribo ATPase (De-Medina et al., Virol. 202:401–407, 1994.)

Heretofore, pX has not been recognized as a target for antiviral therapies, and there is no teaching or suggestion in the prior art of methods for identifying agents that interfere with pX activity in vitro or in vivo. The present invention, by contrast, establishes for the first time that pX activates transcription by binding directly to specific classes of transcription factors, those that contain bZIP domains, thereby promoting dimerization of the factors and increasing their binding to DNA. These surprising findings diverge from all existing reports on the nature of pX activity. Thus, prior to the present invention, there would have been no reason for those skilled in the art to devise screening methods for screening to identify compounds that specifically interfere with pX activity and thus inhibit HBV replication.

SUMMARY OF THE INVENTION

The present invention encompasses a high-throughput screening method to identify inhibitors of Hepatitis B Virus (HBV) replication. The method is carried out by contacting the pX protein of HBV with (i) a transcription factor containing a bZIP domain, or fragments of a transcription factor containing a minimal bZIP domain, and (ii) an oligonucleotide comprising the target DNA sequence of the transcription factor. The reaction components are incubated in the presence of a plurality of test compounds, to form test mixtures, and in the absence of test compounds, to form control mixtures. The mixtures are then incubated under appropriate conditions, and for sufficient time, to allow pX-mediated dimerization and DNA binding of the transcription factor to occur. Thereafter, the level of DNA binding of the transcription factor is determined in each of the test and control mixtures. The DNA binding levels in the test mixtures and control mixtures are then compared. An inhibitor is identified as any test compound that causes a decrease in the level of DNA binding in the test mixture relative to that in a control mixture.

In another aspect, the invention encompasses methods for inhibiting replication of HBV by introducing into infected cells an inhibitor molecule that interferes with the binding of the pX protein of HBV to a bZIP domain in a bZIP-containing protein.

BRIEF DESCRIPTION OF THE DRAWINGS

FIG. 1C shows the binding of a purified GST-ATF2 fusion protein, respectively. In each case, 5, 10, and 20 ng of each affinity purified GST fusion protein were incubated with the $^{32}$P-labelled CRE in the presence of 1 µg of bovine serum albumin (BSA) (–) or 100 ng of affinity purified pX (+). Reaction products were analyzed on a 5% native acrylamide gel in 0.5× Tris-borate EDTA (TBE) buffer.

DETAILED DESCRIPTION OF THE INVENTION

All patent applications, patents, and literature references cited in this specification are hereby incorporated by reference in their entirety. In case of conflict, the present description, including definitions, will control.

Definitions

1. "Protein X" (designated pX) is protein of 16.5 kDa encoded by the genome of Hepatitis B virus (HBV) (Kwee et al., *Virol.* 66:4382, 1992). Two smaller polypeptides of 8 and 6.6 kDa encoded by the same gene have also been detected, and are thought to result from translation initiation at internal AUG codons; these and other pX-derived polypeptides that may be found to exhibit pX activity are also encompassed by the present invention.

2. "pX activity" is defined herein as binding to the basic region of a bZIP-containing transcription factor, enhancement of dimerization of the factor, stimulation of the DNA binding of the dimeriz, and, ultimately, enhancement of the transactivation activity of the factor.

3. An "anti-HBV agent" is defined herein as a compound or composition that interferes with the replication of HBV in vitro or in vivo.

4. A "pX::bZIP binding pair" refers to the interaction between pX and transcription factors that contain bZIP domains. A "bZIP domain" refers to a peptide containing a) a basic region that binds DNA and b) a leucine zipper region that allows two bZIP-containing polypeptides to form dimers. Examples of bZIP-containing transcription factors include CREB, ATF-binding proteins such as ATF-2, C/EB, c-fos, c-jun, NF-κb, and rel (Alber, *Curr. Biol.* 3:182; Karin, *Trends Gen.* 5:65, 1989; Ellenberger, *Curr. Opin. Struc. Biol.* 4:12, 1994; Burley, *Curr. Opin. Struc. Biol.* 4:3–11, 1994; Ziff, *Trends Gen.* 6:69, 1990; Busch et al., *Trends Gen.* 6:36, 1990.) A "minimal bZIP peptide" refers to a fragment of a bZIP-containing protein that retains the capability of interacting with pX and with DNA e.g. a peptide comprising amino acids 350–415 of the ATF2 protein (see Example 1 below).

5. As used herein, "test compound" refers to an agent, comprising a compound, molecule or complex, which is being tested for its ability to inhibit the activity of pX. Test compounds can be virtually any agent, including without limitation peptides, proteins, lipids, polysaccharides, nucleic acids, including small organic molecules, and combinations thereof. Complex mixtures of substances such as natural product extracts, which may include more than one test compound, are also encompassed by this term.

6. As used herein, "oligoduplex" refers to a double-stranded DNA comprised of two complementary oligonucleotides.

7. "High-throughput screening" refers to methods for simultaneously assaying a large number of test compounds for their ability to inhibit pX activity. In general, these methods take advantage of automated equipment.

The present invention encompasses the identification and use of agents that interfere with the biological activity of Protein X (pX) of Hepatitis B Virus (HBV). pX is important for replication of HBV in its preferred target cell, the mammalian hepatocyte. The present invention provides methods for identifying compounds that specifically interfere with the function of pX in vitro and in vivo. These methods are based on the unexpected finding that pX binds to the basic region of bZIP-containing transcription factors, enhancing dimerization of these transcription factors through their leucine zipper domains. The increase in dimerization in turn enhances their binding to DNA and, as a consequence, selectively activates HBV transcriptional promoters and certain cellular promoters. On the basis of these findings (detailed in Example 1 below), compounds that interfere with pX activity are expected to partially or totally inhibit HBV replication in an infected cell.

Inhibition of pX activity is achieved through one of several means. Either the inhibitory compound binds to pX itself, or it binds to the target transcription factor, in a manner that prevents the functional binding of pX itself to the factor or the functional binding of the factor to DNA. In a preferred embodiment, the inhibitory compound binds to pX specifically, thereby inactivating it and directly preventing viral gene expression and viral replication.

The present invention encompasses high-throughput screening methods to identify pX-inhibitory compounds. In one embodiment, the method comprises immobilizing an oligoduplex containing a DNA binding site for a bZIP-containing transcription factor on a solid-phase matrix. This procedure is carried out using techniques that are well-known in the art. Non-limiting examples of suitable matrices include plastic microtiter dishes, and nitrocellulose filters or other types of membranes suitable for binding DNA. The immobilized DNA is then exposed to a reaction mixture containing a) pX protein and b) a bZIP-containing protein or a fragment derived therefrom that retains minimal bZIP activity. Preferably, component b) contains a convenient label e.g. a radioactive, fluorescent, or enzyme-linked moiety that can be easily detected using methods that are standard in the art. The reaction mixture also contains appropriate buffers, salts, blocking agents, and other additives that ensure that a detectable amount of the component described in b) binds specifically, and in a pX-dependent fashion, to the microtiter dish. After incubation under appropriate conditions and for a sufficient time to promote detectable transcription factor binding to the dish, the reaction mixtures are removed, the dishes are washed free of unbound factors, and pX activity is detected as an increase in the level of bound bZIP factors.

In an alternate embodiment, the high-throughput screening method involves mixing pX with a bZIP-containing protein, a bZIP domain, or a minimal bZIP peptide in solution, under appropriate conditions for binding to the bZIP peptide. pX activity is detected as promoting dimerization of the bZIP-containing peptide. This may be carried out by using a pX peptide to which a fluorescent moiety has been conjugated. As increasing amounts of bZIP protein bind pX and dimerize, the molecular rotation of the peptide decreases, leading to an increase in the fluorescence polarization of the reaction mixture.

In both of the above embodiments, assays are performed in the absence and presence of test compounds. Test compounds are prepared as serial three to ten-fold dilutions in solvents or buffers compatible with the assay, and are added prior to, or simultaneous with, the pX protein. A test compound that inhibits pX activity by more than 30% relative to controls is a candidate for an anti-HBV agent.

According to the invention, large numbers of test compounds are assayed in a cost-efficient, rapid manner. Useful agents may be found within numerous chemical classes, though typically they are organic compounds, and preferably small organic compounds. Small organic compounds have a molecular weight of more than 50 yet less than about 2,500 daltons, preferably less than about 750, more preferably less than about 400 daltons. Exemplary compounds include peptides, saccharides, steroids, and the like. The compounds may be modified to enhance efficacy, stability, and pharmaceutical compatibility. Natural product extracts can also be tested, and the component that inhibits pX can be purified from the mixture in a subsequent step.

Test compounds for use in high-throughput screening methods may be found in large libraries of synthetic or natural substances. Numerous means are currently used for random and directed synthesis of saccharide, peptide, and nucleic acid-based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). In addition, there exist methods for generating combinatorial libraries based on peptides, oligonucleotides, and other organic compounds (Baum, *C&EN*, Feb. 7, 1994, page 20–26). Alternatively, libraries of natural compounds in the form of bacterial, fungal, plant and animal extracts are available from e.g. Pan Labs (Bothell, Wash.) or MycoSearch (NC), or are readily producible. Additionally, natural and synthetically produced libraries and compounds are readily modified through conventional chemical, physical, and biochemical means.

In one embodiment, peptides that mimic the bZIP domain of a bZIP-containing transcription factor are tested for their ability to competitively inhibit pX binding to the bZIP-containing factor. In another embodiment, antibodies are tested for their ability to interfere with the formation of the pX::bZIP binding pair. Polyclonal and monoclonal antibodies specific for pX or for bZIP-containing transcription factors can be prepared by methods that are well-known in the art (E. Harlow & D. Lane, *ANTIBODIES: A LABORATORY MANUAL,* Cold Spring Harbor Laboratory, 1988; Zola, *Monoclonal Antibodies: A Manual of Techniques,* CRC Press, Inc., Boca Raton, Fla., 1987). Preferably, the antibody to be used for this purpose is a monoclonal antibody that recognizes pX.

Once a test compound has been identified in vitro as a candidate anti-HBV agent, it is further tested in vitro for its ability to inhibit HBV replication and/or HBV-induced malignant transformation in cell culture and in animal model systems. A typical cell culture system comprises hepatoblastoma cells such as HepG2 cells that have been transfected with copies of the HBV genome (Sells et al., *Proc. Natl. Acad. Sci. USA* 84:1005, 1987), maintained in minimal essential medium supplemented with 10% fetal bovine serum at 37° C. in a moist atmosphere containing 5% $CO_2$ in air. $3\times10^5$ cells are seeded into 25 $cm^2$ tissue culture flasks in the absence and presence of increasing concentrations of the candidate compounds. The candidate compound may be added directly to the culture medium. Alternatively, techniques that are well-known in the art may be used to enhance uptake of the compound by the cells or penetration of the compound across the cell membrane e.g. electroporation, liposome encapsulation, microinjection, or scrape loading. HBV replication is measured by monitoring the levels of intracellular and extracellular HBV DNA, using Southern blotting with radiolabelled HBV-specific probes (Sells et al., *J. Virol.* 62:2836, 1988). A decrease in viral DNA of 40% over that observed in control flasks indicates that the candidate compound is an anti-HBV agent.

Similarly, an animal model system for HBV infection comprises chimpanzees, ground and tree squirrels, Pekin ducks, or, most preferably, woodchucks. Woodchuck hepatitis virus (WHV) infection of its natural host, the eastern woodchuck, has been developed as a model of HBV-induced liver disease in humans. Chronic WHV infection can be predictably established under experimental conditions, and causes progressive liver disease (Ponsetto et al., *Hepatology* 14:16–23, 1991).

Evaluation of candidate anti-HBV agents identified by the high-throughput in vitro screening method described above can also be carried out in this animal model. Viremia, liver disease, and hepatocellular carcinoma are monitored in chronically infected woodchucks in the absence and presence of increasing amounts of the candidate compound. A decrease in viremia of 90% in the animal model indicates that the candidate compound is an anti-HBV agent.

Applications

Compounds identified as anti-HBV agents using the methods of the present invention find different applications in the field of antiviral therapies. First, they may serve as the starting material for the design of anti-HBV agents that are more suitable than the initially identified compound for use in clinical settings. For example, once a peptide anti-HBV agent is identified, it may be systematically modified in a variety of ways to e.g. enhance its stability, solubility properties, potency, etc. Non-limiting examples of potential modifications include introducing an unnatural amino acid, such as a D-amino acid, and particularly D-alanine; and functionalizing the amino or carboxyl terminus by e.g. acylation, alkylation, esterification or amidification. Other modifications include encapsulation in e.g. liposomes, or formation of complexes with other components.

In practicing the present invention, it may be desirable to target a therapeutic compound to the liver. This may be achieved by any of several methods known in the art, including conjugation to an antibody that specifically recognizes liver cells; conjugation to a galactose-terminating oligosaccharide that serves as a ligand for the liver-specific asialoglycoprotein receptor; and incorporation into liposomes.

For therapeutic applications as in e.g. the treatment of HBV infection in mammals, anti-HBV agents identified by the methods of the present invention may be formulated with a physiologically acceptable carrier, e.g. phosphate buffered saline or deionized water. The pharmaceutical formulation may also contain excipients, including preservatives and stabilizers, that are well-known in the art. Modes of administration include oral and enteral, intravenous, intramuscular, subcutaneous, transmucosal (including rectal and buccal), and by inhalation. Generally, the amount of the agent to be administered will be empirically determined, typically in the range of about 10 to 1000 pg/kg of the recipient. For peptide agents, the concentration will generally be in the range of about 100 to 500 ug/ml in the dose administered. It will be understood that the pharmaceutical formulations of the present invention need not in themselves contain the entire amount of the agent that is effective in treating HBV infection, as such effective amounts can be reached by administration of a single dose, or a plurality of doses of such pharmaceutical formulations.

The following examples are intended to further illustrate the invention without limiting it thereof.

EXAMPLE 1

The pX Protein of Hepatitis B Virus Enhances the DNA Binding of bZIP-containing Transcription Factors by Targeting Their Conserved Basic Region The following experiments were performed to investigate the transcription-enhancing activity of the pX protein of Hepatitis B Virus (HBV).

Figure 1A:
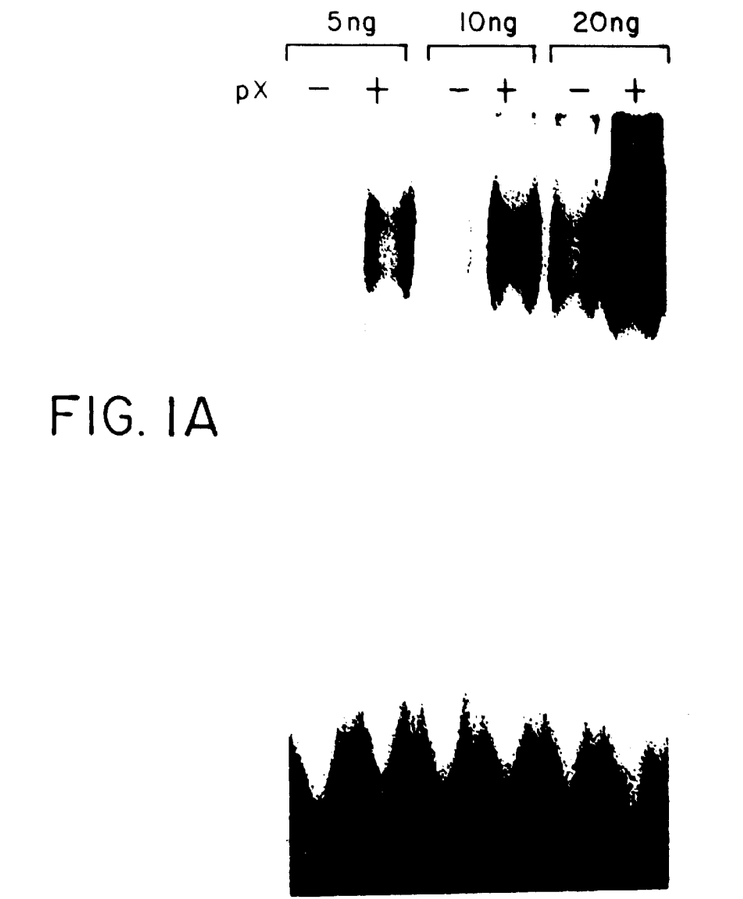
FIG. 1A shows an autoradiogram that demonstrates the binding of a glutathione-S-transferase (GST)-CREB fusion protein to a synthetic $^{32}$P-labelled oligoduplex DNA containing the CRE core site, in the presence or absence of pX as indicated.
Figure 1B:
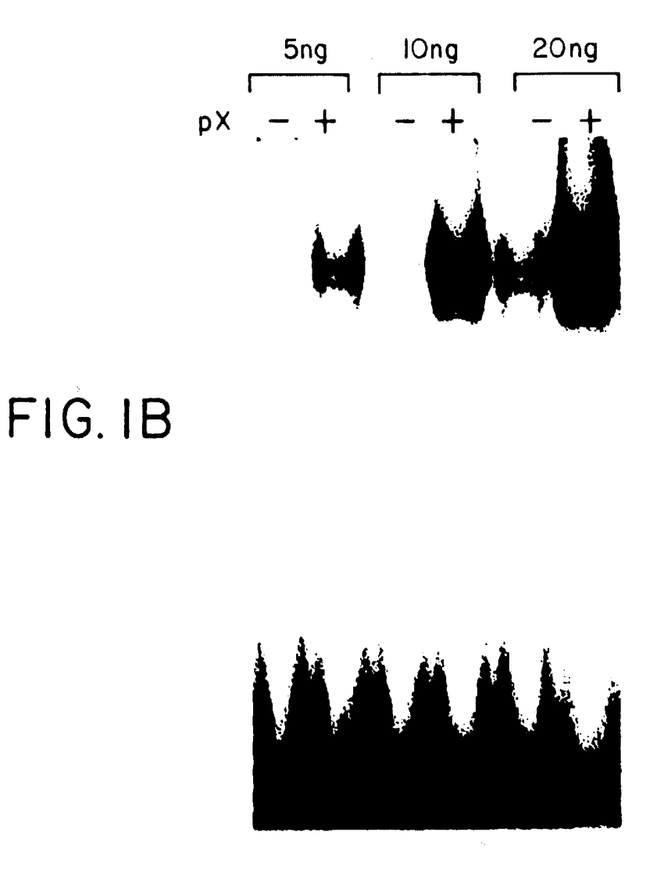
FIG. 1B shows the binding to the same CRE of a purified GST-ATF1 fusion protein.
Figure 1C:
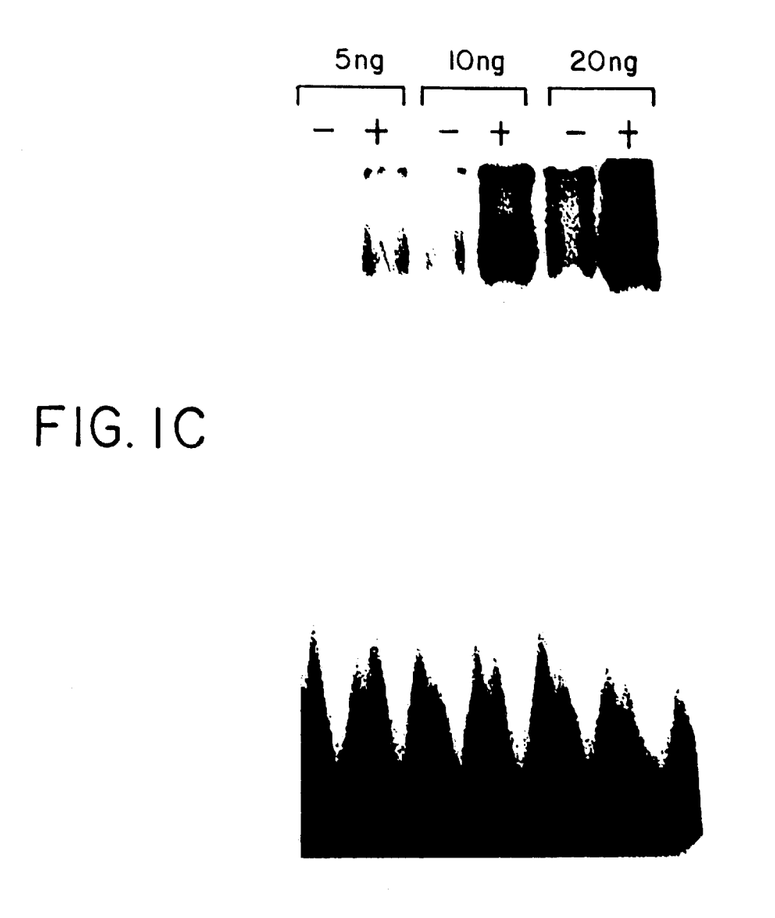

A. pX Increases the DNA Binding Activity of Different bZIP-containing Transcription Factors To investigate the effect of pX on ATF DNA binding activity, the bZIP domains of three ATFs (ATF-1, ATF-2 and CREB) were first purified as glutathione-S-transferase (GST)-fusion proteins using glutathione-agarose beads. Specifically, DNA encoding amino acids 23–341 of CREB, 57–271 of ATF-1, and 144–505 of ATF-2 were cloned into the pGEX-2T vector and expressed in E. coli. The purified fusion proteins were then assayed for binding to a DNA oligoduplex containing the CRE binding site using a standard gel-shift assay (FIGS. 1A–1C). The CRE core binding site has the sequence 5'-TCCTAAGTGACGTCAGTGGAA-3' SEQ ID NO:1. DNA binding reactions were performed using protein concentrations that gave rise to a low level of DNA binding in the absence of pX. More specifically, binding reactions contained approximately 5 to 20 ng of affinity-purified fusion protein and approximately 100 ng pX protein.

pX protein was produced as follows: pX was expressed in E. coli strain BL21(pLysE) transformed with the pRSET-C vector into which DNA encoding pX had been cloned. The transformed cells were grown at 30° C. in the presence of 50 $\mu$M $ZnCl_2$, and pX expression was induced by addition of 1 mM IPTG. Cells were harvested and resuspended in lysis buffer (1M NaCl, 20% glycerol, 0.1% Tween-20, 20 mM Tris-HCl pH 8, 20 $\mu$M $ZnCl_2$, 1 mM phenylmethylsulfonylchloride, and 10 mM β-mercaptoethanol). After sonication, the bacterial lysate was subjected to centrifugation for 30 min at 12,000 rpm, and the supernatant was recovered and incubated with NTA $Ni^{+2}$ beads (Qiagen, Inc.) for several hours. The beads were washed extensively with lysis buffer, after which pX was eluted with 0.5M imidazole pH 7.5. The eluted pX protein was dialyzed against buffer X (0.2M NaCl, 20% glycerol, 20 mM Hepes pH 8, 20 $\mu$M $ZnCl_2$, 5 mM β-mercaptoethanol, 0.1% Tween-20, and 1 mM phenylmethylsulfonylchloride.)

Under the conditions described above, addition of purified pX greatly increased DNA binding of CREB, ATF-1, and ATF-2. As expected, there was no detectable interaction between purified pX and DNA in the absence of added transcription factors. Addition of E. coli crude extract or an unrelated transcription factor (hTFIIB) purified from E. coli had no effect on DNA binding of GST-ATF1, indicating that the effect of pX on DNA binding was not due to a co-purified contaminant from E. coli.

B. pX-Mediated Enhancement of DNA Binding is Specific for bZIP Proteins

To assess the specificity of pX-mediated enhancement of DNA binding, a gel-shift assay was used to test several other well-characterized transcription factors for the ability of pX to influence their binding to their cognate DNAs. The AP-1 family of transcription factors are related to ATF proteins (20–30% similar; reviewed by Angel and Karin, Biochim. Biophys. Acta 1072:129, 1991). AP-1 proteins also contain bZIP domains and bind a DNA sequence (5'-TGACTCA-3'), which differs in only one position from an ATF consensus site (5'-TGACGTCA-3'). c-Jun is a prototype AP-1 protein.

Figure 2A:
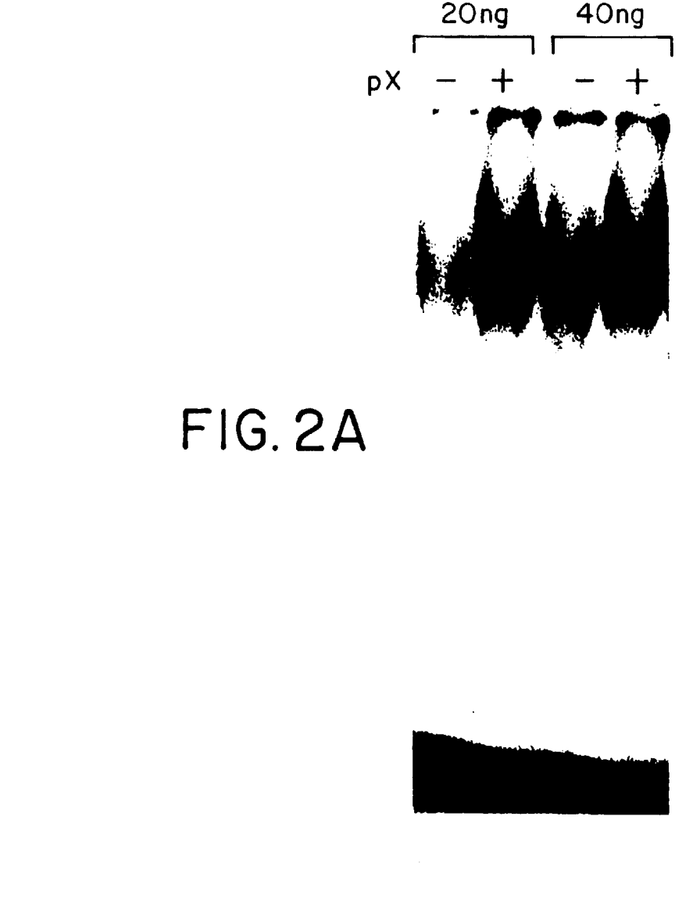
FIG. 2A shows an autoradiogram demonstrating the binding of 20 and 40 ng of a bacterially expressed C/EBP Δ1–2 derivative to a C/EBP-specific DNA binding site, in the presence or absence of pX as indicated.
Figure 2B:
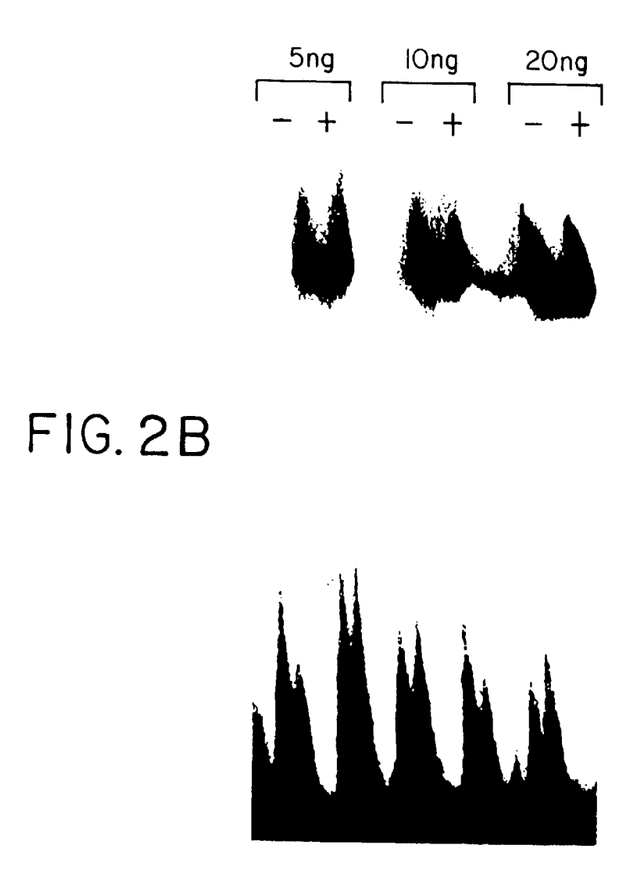
FIG. 2B shows the binding of 5, 10, and 20 ng of a histidine-tagged Jun derivative to the collagenase TRE site.
Figure 2C:
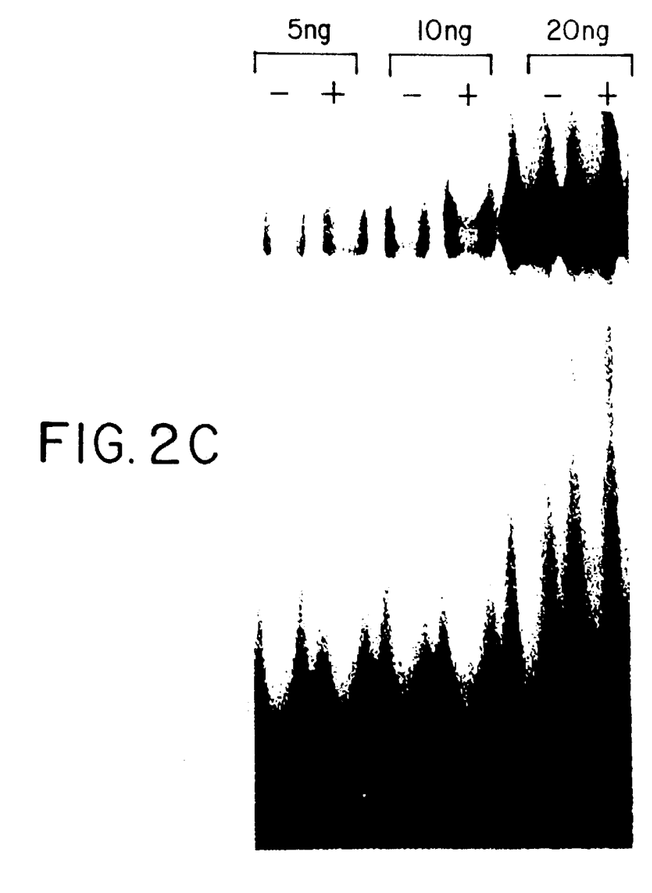
FIG. 2C shows the binding of an affinity purified GST-ATF4 fusion protein to the CRE described in FIG. 1. Reactions were performed and analyzed as in FIG. 1.

The ability of a His-tagged c-Jun fusion protein (Patel et al., Proc. Natl. Acad. Sci. USA 91:7360, 1994) to bind to the collagenase TRE site (5'-AGCTTTGACTCATCCCGGA-3' SEQ ID NO:2) was enhanced by pX in a manner similar to that observed with bacterially expressed ATFs (FIG. 2B). The binding of C/EBP, another distantly related protein (Landschulz et al., Science XXX: 1681, 1989) to its cognate binding site (5'-TGCAGFATTGCGCAATCTGCA-3' SEQ ID NO:3) was also enhanced by pX (FIG. 2A). Thus, stimulation of DNA binding activity by pX appears to be specific for proteins containing a bZIP motif. Additionally, the fact that DNA binding of protein derivatives lacking the GST moiety, such as C/EBP and c-jun, was comparably enhanced by pX, excludes the possibility that the GST moiety was involved in the pX-mediated DNA binding increase observed for GST-ATF fusion proteins. Surprisingly, pX did not increase the binding of ATF4 to the CRE oligoduplex (FIG. 2C), suggesting that the binding of not all bZIP proteins is stimulated by pX.

C. pX Functions through a Minimal bZIP Domain

Figure 3A:
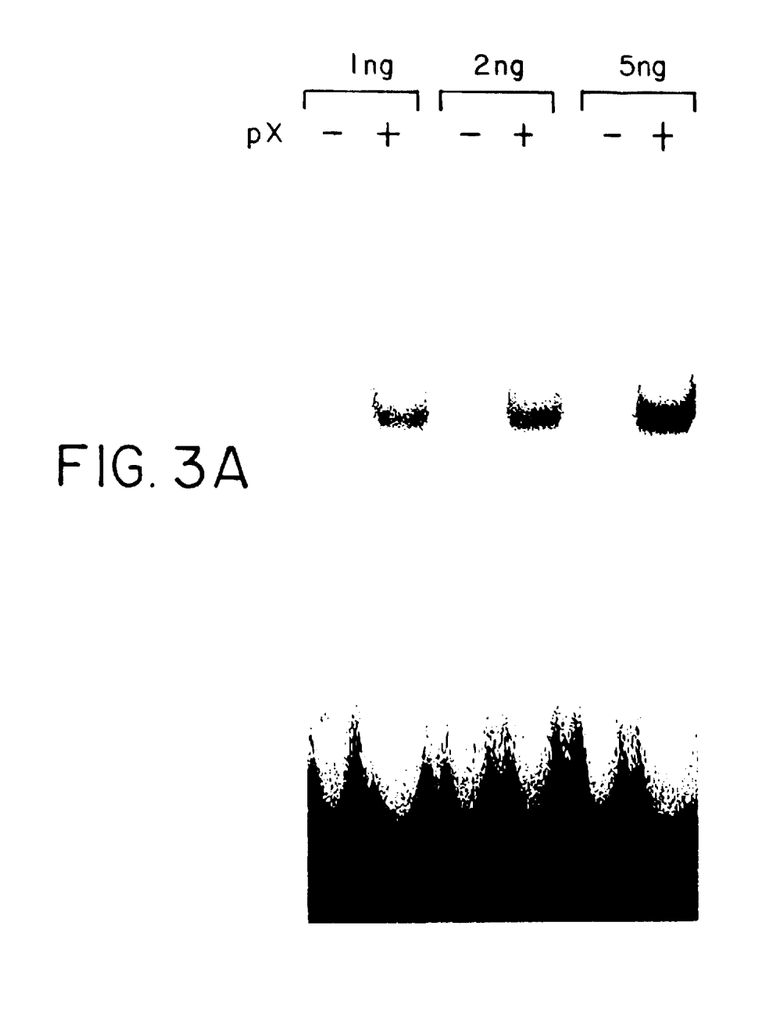
FIG. 3A shows an autoradiogram demonstrating the binding to its cognate DNA of a minimal bZIP domain of ATF-2 expressed as a GST fusion protein.
Figure 3B:
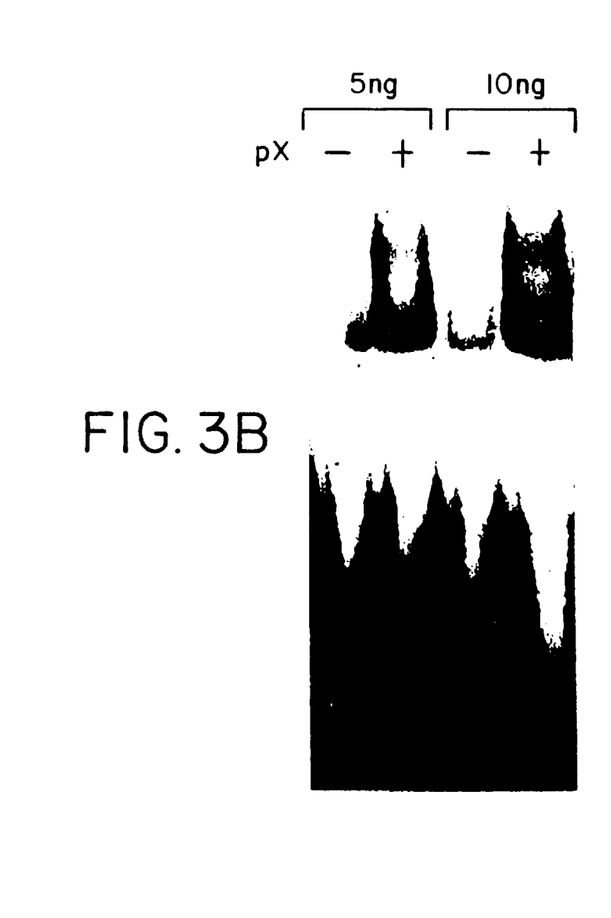
FIG. 3B shows the binding of an analogous minimal bZIP domain derived from c-Jun.
Figure 3C:
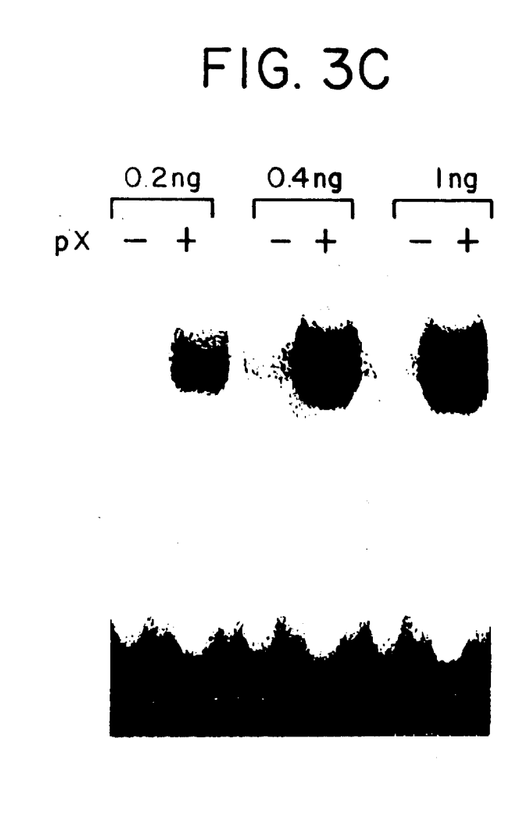
FIG. 3C shows the binding of a minimal bZIP domain of GCN4, both expressed as GST fusion proteins, to their cognate DNA binding sites, respectively. pX protein was added as indicated. Reactions were performed and analyzed as in FIG. 1.

To define the portion of transcription factors required for pX-responsiveness, several GST-fusion polypeptides containing minimal bZIP domains were analyzed. A GST-ATF2 fusion containing the minimal bZIP domain (amino acids 350–415) supported the pX-mediated increased in DNA binding (FIG. 3A). Similarly, DNA binding of a GST-Jun fusion (amino acids 248–320) and a synthetic peptide corresponding to the minimal bZIP region of GCN4 (amino acids 228–281) was enhanced by pX. These results are consistent with the fact that pX increased DNA binding of multiple ATFs, and that the bZIP region is the only region of significant homology among ATF proteins.

D. The Basic Region of the bZIP Domain is the Primary Target of pX

The bZIP-containing proteins function as homo-heterodimers and are characterized by the presence of two conserved regions: one region that rich in basic amino acids that contacts DNA (basic region), and a second region that contains a leucine repeat (leucine zipper) that functions as a dimerization interface. To further define which of the two regions is more important in the interaction between pX and the bZIP-containing proteins, a series of fusion proteins were analyzed.

Figure 5A:
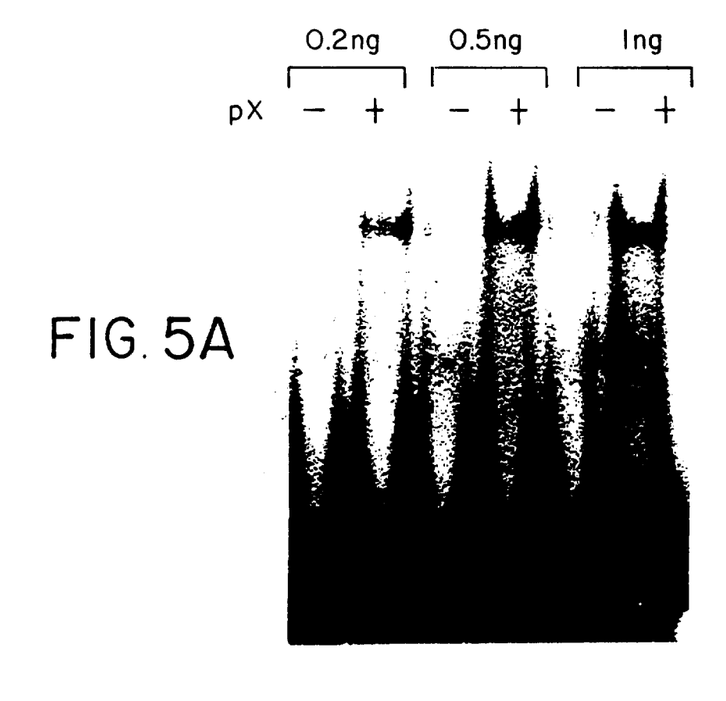
FIG. 5A shows an autoradiogram demonstrating binding of a synthetic bZIP-containing peptide, BR-CC, to the collagenase TRE oligoduplex.

BR-CC is a synthetic peptide having the sequence ALKRARNTEAARRSRARKLQRMKQLED-VKELEEKLKALEEKLKALEEKLKALG SEQ ID NO:4 that contains the wild-type GCN4 basic region fused to an idealized leucine zipper (O'Neil et al., Science 249:774, 1990). In this case, the DNA target was the collagenase TRE element. The idealized leucine zipper was designed to change most of the amino acids between the leucines while maintaining the leucines at their original positions and allowing efficient dimerization of the peptide. FIG. 5A shows that pX stimulated the binding of BR-CC to the TRE.

Figure 5B:
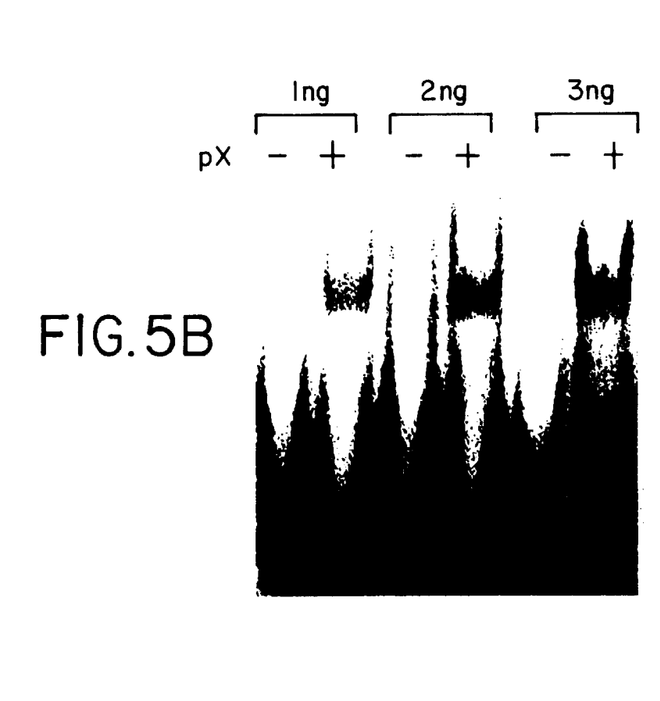
FIG. 5B shows the binding of a minimal bZIP domain of the Epstein Barr virus ZTA protein to the identical TRE.
Figure 5C:
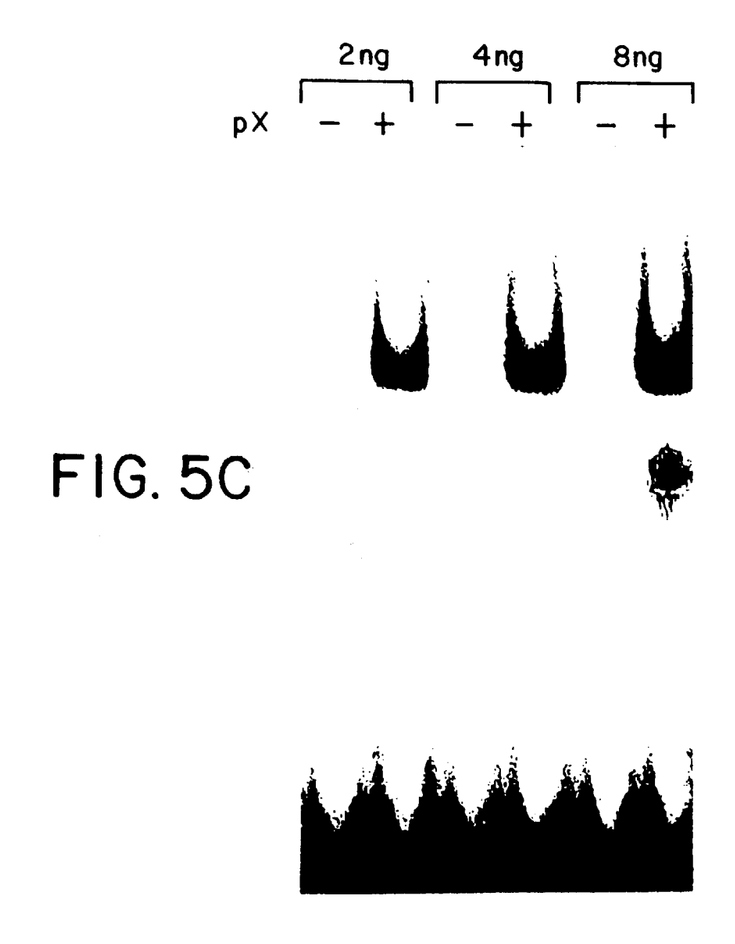
FIG. 5C shows the binding of a chimeric GST-Fos-ZTA protein to the TRE. pX protein was added as indicated.

FIG. 5B shows that the EBV ZTA protein, a highly divergent member of the bZIP family, is also responsive to pX. Although ZTA contains a basic region partially homologous to that of the proteins of the AP-1 family, its dimerization domain does not contain the leucine repeat typical of the leucine zipper proteins. Instead, this domain forms a coiled-coil structure. FIG. 5B shows that pX can stimulate the binding of amino acids 175–229 of ZTA to the collagenase TRE element. Similarly, pX can increase the binding of a chimera containing the c-Fos basic region (amino acids 133–162) fused to the ZTA coiled-coil domain (amino acids 197–229) (FIG. 5C). Taken together, these results indicate that pX does not require a conserved leucine zipper for its activity, and further suggest that the basic region of bZIP-containing transcription factors is an important recognition element for pX.

Figure 6:
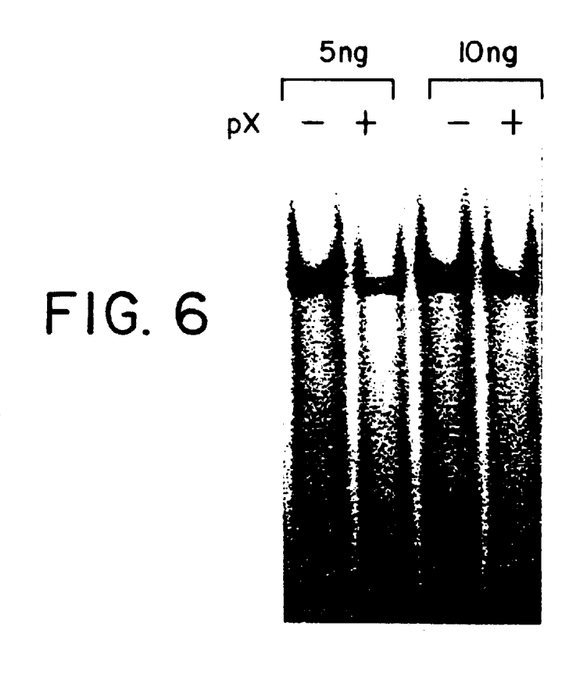
FIG. 6 shows an autoradiogram demonstrating lack of pX-induced binding of a lambda repressor-GCN4 fusion protein (λ-ZIP) to the OR1 site of the λ phage PRM/PR promoter. pX protein was added as indicated.

In support of this hypothesis, a protein lacking the basic region but containing the leucine zipper region is not pX-responsive. A λ-ZIP protein that contains the DNA binding domain of λ repressor (amino acids 1–101) fused in frame to the GCN4 leucine zipper (amino acids 250–281) is not pX-responsive, even when pX is present at high concentration (FIG. 6).

Figure 7:
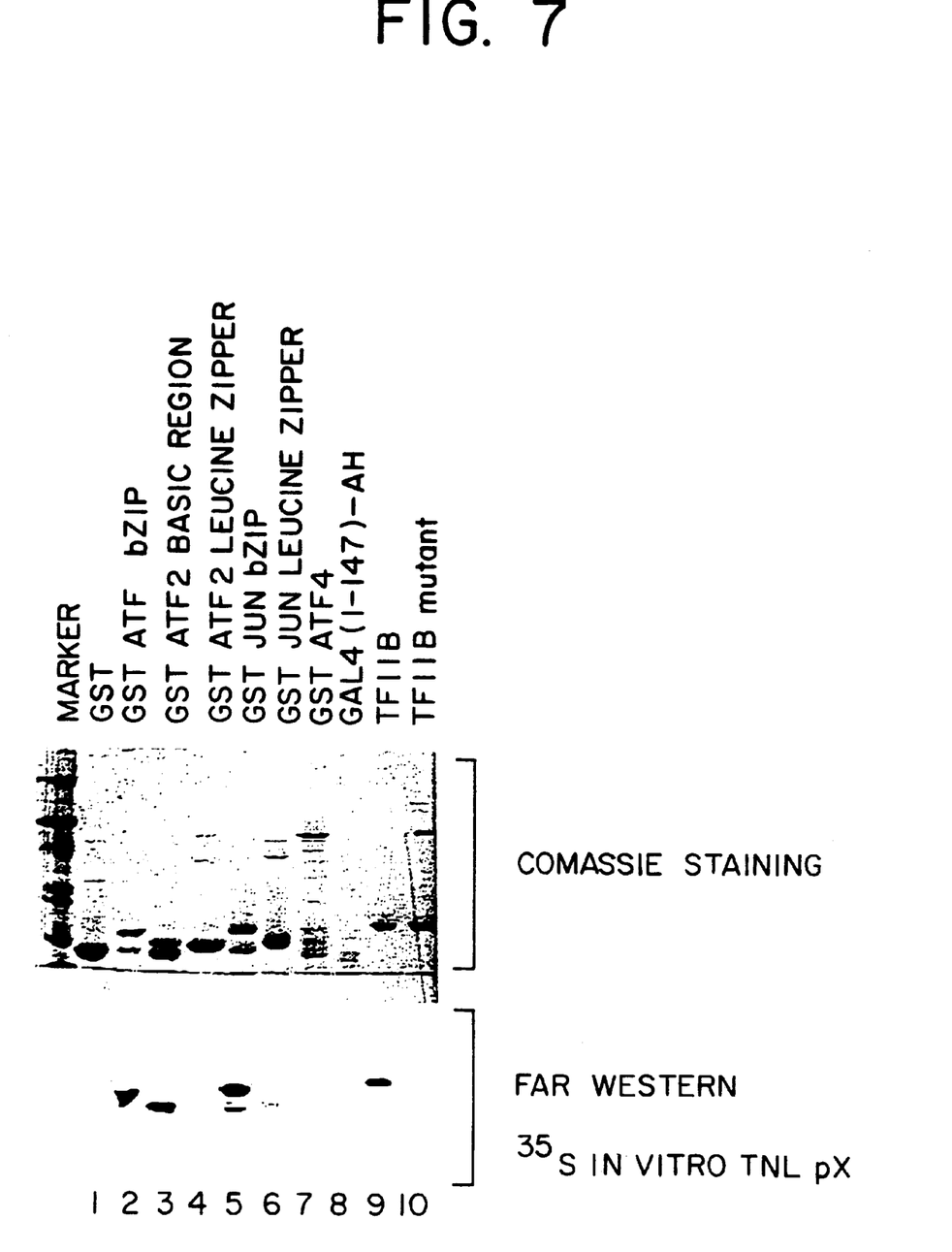
FIG. 7 shows the results of an experiment in which bZIP-containing and other proteins were resolved by SDS-gel electrophoresis. In one case, the proteins were detected by staining with Coomassie blue (top panel.) Proteins resolved in a parallel gel were transferred to an Immobilon membrane, and incubated with $^{35}$S-labelled pX protein (bottom panel).

Further confirmation of the importance of the basic region is shown in FIG. 7. A series of proteins were fractionated on an SDS gel and probed with $^{35}$S-labelled in vitro-translated pX protein. Only those bZIP proteins containing an intact basic region bound pX. By contrast, proteins with leucine zippers alone did not bind pX.

Figure 8:
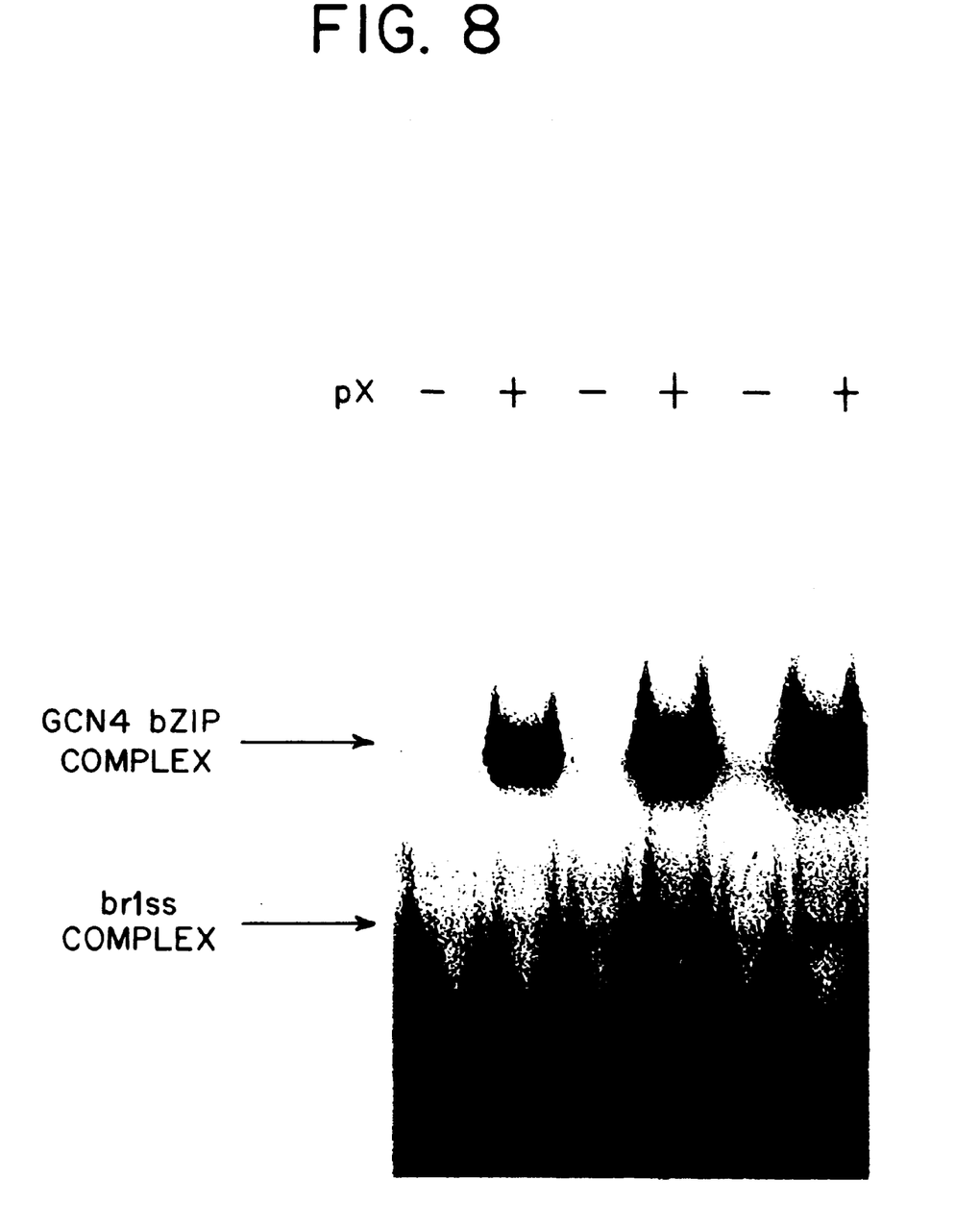
FIG. 8 shows an autoradiogram demonstrating lack of pX-induced binding of a peptide comprising the GCN4 basic region alone (br1ss), and pX-induced binding of the entire GCN4 bZIP region, to the collagenase TRE oligoduplex. pX was added as indicated.

Although the basic region appears to be the most important element in pX-responsiveness, it alone is insufficient. For example, ATF-4, which contains a basic region, does not respond to pX. (This result may be explained by the significant differences between the ATF-4 basic region and that of other ATF proteins.) In addition to ATF-4, a peptide containing the GCN4 basic region alone, having the sequence ALKRARNTEAARRSRARKLQRMKQGGC (designated br1ss SEQ ID NO:5) is also not a target for pX-mediated stimulation of DNA binding (FIG. 8).

FIG. 7 also illustrates another potential drug screening target: the interaction between pX and the general transcription factor TFIIB. This experiment indicates that, in addition to stimulation of DNA binding, pX stimulates transcription by acting as a bridge between the bZIP proteins and the general transcription factors. That is, pX can serve as an adaptor protein by binding to both a gene-specific transcription factor and to a general transcription factor.

Figure 4:
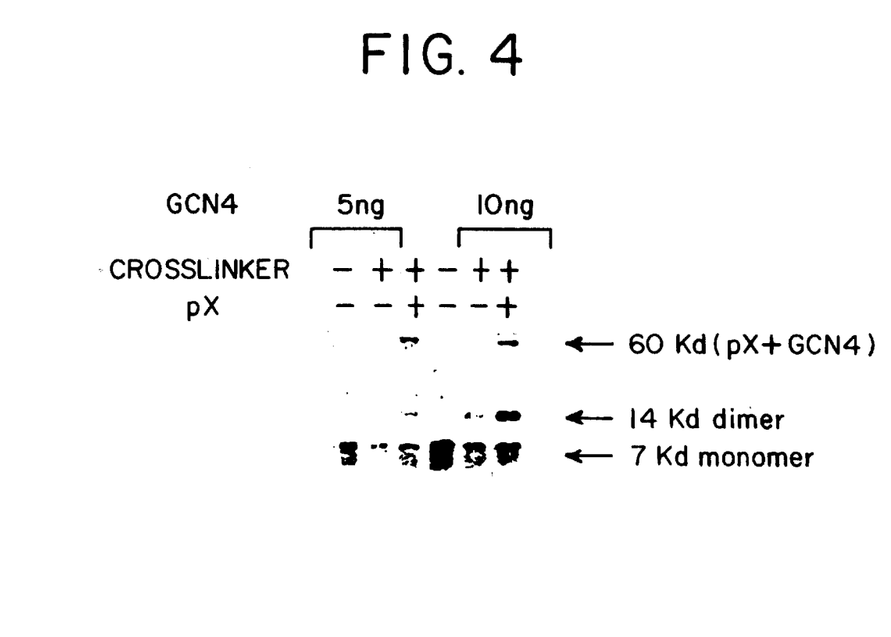
FIG. 4 shows an SDS-polyacrylamide gel showing that pX promotes the formation of dimers of a minimal bZIP peptide from GCN4. The peptide was incubated in the presence of 0.02% glutaraldehyde, with the addition of 200 ng BSA (lanes 1, 2, 4, and 5) or 100 ng pX (lanes 3 and 6). After incubation for 30 min at room temperature, the reaction mixtures were resolved on a 15% SDS-polyacrylamide gel and detected by immunobloting with a GCN4-specific polyclonal antiserum.

E. pX Increases Formation of bZIP Homodimers in the Absence of DNA bZIP proteins bind DNA as dimers, and dimerization is a prerequisite for DNA binding. pX could therefore stimulate DNA binding by increasing either dimerization of the bZIP or the subsequent interaction between the bZIP homodimer and DNA. The effect of pX on dimerization of the bZIP domain was measured using a well described chemical cross-linking assay (FIG. 4).

Previous studies have shown that the subunits of bZIP dimers can be crosslinked to one another with glutaraldehyde, a bifunctional crosslinking reagent. GCN4 peptide (5–10 ng) was incubated in the presence or absence of pX (100 ng). Following addition of glutaraldehyde (0.02% final concentration), the products were fractionated on a SDS-polyacrylamide gel and analyzed by immunoblotting with a GCN4-specific polyclonal antiserum. In the absence of pX, homodimer formation by GCN4 peptide was concentration-dependent. Significantly, addition of pX dramatically increased the amount of GCN4 homodimers at each concentration. Additional crosslinked products were detected, which included pX. These results indicate that pX increases DNA binding activity by a novel mechanism in which pX promotes homodimerization in the absence of DNA. The elevated concentration of the bZIP homodimer results in increased DNA binding.

F. Conclusions

These experiments demonstrate for the first time that pX enhances the DNA binding of bZIP-containing transcription factors. This is accomplished by binding of pX to the basic region of these factors, resulting in a stimulation of dimerization of the factors. Previous reports, by contrast, suggested that pX activates transcription indirectly, acting e.g. through protein kinase or phosphatase or other cellular signal transduction pathways. The present findings thus enable the design of screening methods for compounds that interfere with the activity of pX and thus are effective anti-HBV agents.

EXAMPLE 2

High-throughput Screening of Test Compounds for HBV Inhibitors

A. Binding of DNA to a solid-phase matrix

A biotinylated synthetic oligoduplex containing the CRE core site (5'-biotin-TCCTAAGTGACGTCAGTGGAA-3' SEQ ID NO:1) is bound to the wells of a 96-well microtiter dish in the following manner. A 5 µg/ml solution of avidin is prepared in coupling buffer (which contains, per liter, 1.6 g $Na_2CO_3$, 2.9 g $NaHCO_3$, and 0.9 g $NaN_3$). 200 µl of this solution is added to each well of a Corning microtiter dish, which is then incubated for 12 h at 4° C. The solution is removed, and non-specific binding sites on the wells are blocked with 1% skim milk in phosphate-buffered saline (PBS) for 1 h at 37° C. The blocking buffer is discarded, and the biotin-labelled CRE core oligoduplex is added to the wells (1 pmol/well) and incubated for 30 min at room temperature. The oligonucleotide solution is then removed, and the wells are washed with 1% milk in PBS.

B. Formation of test and control mixtures

After removal of the wash solution, the following components are added to each well: 25 µl of pX (obtained as described in Example 1) at a concentration of 4 µg/ml, diluted fresh in 0.5× Buffer D (50 mM Tris-HCl pH 7.5, 10% glycerol, 1 mM EDTA, 1 mM DTT, 50 mM KCl); 1 µg poly dI-dC; 200 µg/ml bovine serum albumin (BSA); and 20 µl partially purified GST-CREB (amino acids 23–341) that had been labelled with $^{35}$S-methionine either metabolically or by in vitro translation.

Test mixtures contain, in addition to the above components, 5 µl of a 200 µM stock of synthetic organic compounds dissolved in dimethylsulfoxide (DMSO) (Maybridge). Control mixtures are formed by adding 5 µl of DMSO in place of the test compounds.

C. Incubation and washing steps

The plates are incubated for 30 min at room temperature. The contents of each well are then removed by aspiration, and the wells are washed three times with the milk/PBS solution.

D. Detection and Analysis

50 μl of scintillation cocktail is then added to the wells, and the samples are counted in a Wallac Microbeta liquid scintillation counter.

Binding of GST-CREB to the CRE-containing oligoduplex in the wells is found to be dependent on the presence of pX. Compounds that inhibit binding of GST-CREB to the wells by more than 30% are identified, and then tested for their ability to inhibit HBV replication in cell culture and animal model systems.

EXAMPLE 3

High-throughput Screening of Test Compounds for HBV Inhibitors in Solution Using Fluorescence Polarization Detection of DNA Binding A. Formation of test and control mixtures The following components are added to each well of a microtiter dish:

(1) 25 μl of a mixture of (a) pX at a concentration of 4 μg/ml, diluted fresh in 0.5× Buffer D containing 1 μg poly dI-dC and 200 μg/ml BSA; (b) fluorescein-labelled synthetic oligoduplex containing the CRE core site (5'-fluorescein-TCCTAAGTGACGTCAGTGGAA-3' SEQ ID NO:1) at a concentration of 4 ng/ml; and (2) 20 μl of partially purified GST-CREB (amino acids 23–341) at a concentration of 500 ng/ml, diluted fresh in 0.5× Buffer D containing 1 μg poly dI-dC and 200 μg/ml BSA.

Test mixtures contain, in addition to the above components, 5 μl of a 200 μM stock of synthetic organic compounds dissolved in dimethylsulfoxide (DMSO) (Maybridge). Control mixtures are formed by adding 5 μl of DMSO in place of the test compounds.

B. Incubation and washing steps

The plates are incubated for 30 min at room temperature.

C. Detection and analysis

Fluorescence is measured in a 96-well polarimeter. As increasing amounts of protein bind to the labelled DNA, the molecular rotation of the oligonucleotide decreases, leading to an increase in the fluorescence polarization of the mixture.

Binding of GST-CREB to the CRE-containing oligoduplex is found to be dependent on the presence of pX. Compounds that inhibit binding of GST-CREB by more than about 30% are identified, and subsequently tested for their ability to inhibit HBV replication in cell culture and animal model systems.

EXAMPLE 4

High-throughput Screening of Test Compounds for HBV Inhibitors in Solution Using Antibodies to GST A. Binding of anti-GST antibodies to a solid-phase matrix Corning 96-well dishes are coated with anti-GST antibodies (1.0 μg/well) by incubating anti-GST antibodies (200 μl of a 5 μg/ml stock) in coupling buffer (which contains, per liter, 1.6 g Na$_2$CO$_3$, 2.9 g NaHCO$_3$, and 0.9 g NaN$_3$) in the well for 12 h at 4° C. The buffer is removed by aspiration, and nonspecific binding sites on the wells are blocked with 1% skim milk in PBS for 1 h at 37° C.

B. Formation of Test and Control Mixtures

After removal of the wash solution, the following components are added to each well:

(1) 25 μl of a mixture of (a) pX at a concentration of 4 μg/ml, diluted fresh in 0.5× Buffer D containing 1 μg poly dI-dC and 200 μg/ml BSA; (b) $^{32}$P-labelled synthetic oligoduplex containing the CRE core site (5'-TCCTAAGTGACGTCAGTGGAA-3' SEQ ID NO:1) at a concentration of 4 ng/ml; and (2) 20 μl of partially purified GST-CREB (amino acids 23–341) at a concentration of 500 ng/ml, diluted fresh in 0.5× Buffer D containing 1 μg poly dI-dC and 200 μg/ml BSA.

Test mixtures contain, in addition to the above components, 5 μl of a 200 μM stock of synthetic organic compounds dissolved in dimethylsulfoxide (DMSO) (Maybridge). Control mixtures are formed by adding 5 μl of DMSO in place of the test compounds.

C. Incubation and washing steps

The plates are incubated for 30 minutes at room temperature. Samples are then removed, and the wells are washed three times with the PBS/milk solution.

D. Detection and analysis

50 μl of scintillation cocktail is added to the wells, and samples are counted in a Wallac Microbeta liquid scintillation counter.

Binding of GST-CREB to the labelled oligonucleotide in the wells is detected by capture of the GST-CREB-DNA complex by the anti-GST antibody. Binding of of GST-CREB to the labelled oligonucleotide is found to be dependent on the presence of pX. Compoounds that inhibit binding of GST-CREB by more than about 30% are identified, and tested for their ability to inhibit HBV replication in cell culture and animal model systems.

EXAMPLE 5

High-throughput Screening of Test Compounds for HBV Inhibitors in Solution Using Fluorescence Polarization Detection of Protein Complex Formation in the Absence of DNA A. Formation of test and control mixtures The following components are added to each well of a microtiter plate:

(1) 25 μl of a mixture of pX at a concentration of 4 μg/ml, diluted fresh in 0.5× Buffer D containing 1 μg poly dI-dC and 200 μg/ml BSA; and (2) 20 μl of fluorescently labelled synthetic bZIP peptide (consisting of amino acids 222–281 of GCN4) at a concentration of 500 ng/ml, diluted fresh in 0.5× Buffer D containing 1 μg poly dI-dC and 200 μg/ml BSA.

Test mixtures contain, in addition to the above components, 5 μl of a 200 μM stock of synthetic organic compounds dissolved in dimethylsulfoxide (DMSO) (Maybridge). Control mixtures are formed by adding 5 μl of DMSO in place of the test compounds.

B. Incubation and washing steps

The plates are incubated for 30 min at room temperature.

C. Detection and analysis

Fluorescence is measured in a 96-well polarimeter. As increasing amounts of bZIP protein bind pX and dimerize, the molecular rotation of the peptide decreases, leading to an increase in the fluorescence polarization of the reaction mixture.

Dimerization of bZIP peptide in the wells is found to be dependent on the presence of pX. Compounds that inhibit dimerization by more than about 30% are identified. Compounds are then tested for their ability to inhibit HBV replicatin in tissue culture and animal model systems.

What is claimed is:

1. A high-throughput screening method for identifying inhibitors of Hepatitis B Virus pX activity, which comprises the steps of:
   a) contacting purified pX protein of HBV with (i) a purified transcription factor comprising a bZIP domain, or fragments thereof comprising a minimal bZIP domain, and (ii) a purified oligoduplex comprising a target DNA sequence of said transcription factor, in the presence of a plurality of test compounds, to form test mixtures;
   b) contacting said pX protein with said transcription factor and said oligoduplex in the absence of test compounds, to form control mixtures;
   c) incubating said test mixtures and said control mixtures under appropriate conditions and for a sufficient time to allow pX-mediated dimerization and DNA binding of said transcription factor to occur;
   d) determining the level of DNA binding of said transcription factor in each of said mixtures;
   e) comparing the level of DNA binding in the test mixtures with the level in the control mixtures; and
   f) selecting as an inhibitor of pX activity any test compound that causes a decrease in the level of DNA binding in the test mixture relative to the level of DNA binding in the control mixture.

2. The method of claim 1 wherein the test compound is selected from the group consisting of a peptide, an antibody, and a small organic molecule.

3. The method of claim 1 wherein the transcription factor is selected from the group consisting of ATF and AP-1 proteins.

4. The method of claim 3 wherein the AP-1 protein is selected from the group consisting of c-fos and c-jun.

5. The method of claim 1 wherein the oligonucleotide is immobilized on a solid-phase support.

6. The method of claim 1, wherein the oligonucleotide further comprises a detectable labelled moiety.

7. The method of claim 6, wherein said moiety is selected from the group consisting of a radioactive moiety and a fluorescent moiety.

8. A high-throughput screening method for identifying inhibitors of Hepatitis B Virus pX activity, which comprises the steps of:
   a) contacting purified pX protein of HBV with a purified transcription factor comprising a bZIP domain, or fragments thereof comprising a minimal bZIP domain, in the presence of a plurality of test compounds, to form test mixtures;

b) contacting said pX protein with said transcription factor in the absence of test compounds, to form control mixtures;

c) incubating said test mixtures and said control mixtures under appropriate conditions and for a sufficient time to allow pX-mediated dimerization of said transcription factor to occur;

d) determining the level of dimerization of said transcription factor in each of said mixtures;

e) comparing the level of dimerization in the test mixtures with the level in the control mixtures; and f) selecting as an inhibitor any test compound that causes a decrease in the level of dimerization in the test mixture relative to the level of dimerization in the control mixture.

9. The method of claim 8 wherein the test compound is selected from the group consisting of a peptide, an antibody, and a small organic molecule.

10. The method of claim 8 wherein the transcription factor is selected from the group consisting of ATF and AP-1 proteins.

* * * * *